(12) United States Patent
Krumme

(10) Patent No.: US 7,332,230 B1
(45) Date of Patent: Feb. 19, 2008

(54) MULTILAYER PREPARATION IN FILM FORM, CONSISTING OF HYDROPHILIC POLYMERS, FOR THE RAPID RELEASE OF ACTIVE INGREDIENTS

(75) Inventor: Markus Krumme, Neuwied (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 400 days.

(21) Appl. No.: 10/129,835

(22) PCT Filed: Nov. 3, 2000

(86) PCT No.: PCT/EP00/10856

§ 371 (c)(1),
(2), (4) Date: Jul. 10, 2002

(87) PCT Pub. No.: WO01/34121

PCT Pub. Date: May 17, 2001

(30) Foreign Application Priority Data

Nov. 11, 1999 (DE) ................................ 199 54 245

(51) Int. Cl.
| | |
|---|---|
| A61F 13/00 | (2006.01) |
| A61F 47/00 | (2006.01) |
| A61K 47/34 | (2006.01) |
| A61L 15/16 | (2006.01) |
| B32B 27/08 | (2006.01) |

(52) U.S. Cl. ...................... 428/516; 428/520; 424/434; 424/439; 424/435; 424/444; 424/426; 514/772.2

(58) Field of Classification Search ................ 424/434, 424/439, 408, 413, 480, 435, 444, 407, 426, 424/495; 514/772.2, 781; 428/147, 516, 428/520, 420, 424.6
See application file for complete search history.

(56) References Cited

U.S. PATENT DOCUMENTS 5,700,478 A 12/1997 Biegajski et al.

FOREIGN PATENT DOCUMENTS

| EP | 0 781 546 A | 7/1997 |
|---|---|---|
| JP | 63 171565 A | 7/1988 |
| WO | 98 17251 A | 4/1998 |

*Primary Examiner*—Rena Dye
*Assistant Examiner*—Lawrence Ferguson
(74) *Attorney, Agent, or Firm*—Birch, Stewart, Kolasch & Birch, LLP

(57) ABSTRACT

A multilayer preparation in the form of films of hydrophilic polymers for rapid release of substances present in the film layers into liquid surroundings is characterized in that adjacent layers differ from one another in that in each case one layer is soluble in a nonaqueous solvent in which the respective adjacent layer is insoluble or only slightly soluble.

32 Claims, No Drawings

MULTILAYER PREPARATION IN FILM FORM, CONSISTING OF HYDROPHILIC POLYMERS, FOR THE RAPID RELEASE OF ACTIVE INGREDIENTS

This application is the national phase under 35 U.S.C. § 371 of PCT International Application No. PCT/EP00/10856 which has an International filing date of Nov. 3, 2000, which designated the United States of America.

BACKGROUND OF THE INVENTION

1. Field of the Invention

The invention relates to a multilayer preparation in the form of films of hydrophilic polymers which is suitable for delivering the substances present therein to the surroundings within a short time. The invention relates in particular to preparations of the type mentioned, whose layers contain pharmacologically active substances. The invention further relates to a process for producing such preparations, and to the use thereof.

2. Description of the Related Art

In systems for delivering active ingredients, in particular in pharmaceutical forms, it is necessary in relation to certain areas of use for a relatively large amount of a pharmacologically active substance to be released in the human or animal body within a short time. This can be achieved, for example, by aiming in the formulation of the pharmaceutical form at a surface area which is as large as possible by comparison with the volume. In accordance with the laws of diffusion, this increases the rate of delivery of the constituents to the surroundings.

However, there are limits to increasing the surface area because the substance-delivering composition must, on the other hand, also be as compact as possible in order to confer adequate strength on the system and make handling easily possible. Thus, for example, the area of oral dosage forms cannot be increased indefinitely.

The requirement for rapid release of active ingredient with, at the same time, compactness is met by dosage forms in the form of films which contain the active ingredients in dissolved, emulsified or suspended form. Because the dimension in the direction of the thickness of the film is relatively small, the diffusion pathways are short and thus the times required for dissolution are also short, so that high rates of release can be achieved.

It is known to produce such films from hydrophilic polymers as film-forming agent, where appropriate with the addition of auxiliaries to adjust the physicochemical parameters of the film, the chemical stability and/or the taste. Such films can be obtained by producing a solution which contains the polymer matrix in a hydrophilic solvent, usually water. This solution is mixed with active ingredients and auxiliaries and coated onto a processing sheet made of plastic or metal. The solvent is removed by subsequent drying, and the polymer matrix remains behind as film. However, only a certain maximum film thickness can be achieved with this process, the kinetics of drying representing the limiting factor. The possible rate of coating particularly for aqueous systems is, owing to the relatively high heat of vaporization, relatively low in coupled coating and drying machines, so that there are corresponding limits on the film thickness which can be achieved in this way.

It is true that such relatively thin films have the advantage that they are relatively rapidly dissolved in the body and thus bring about rapid release of active ingredient. However, since the mode of production limits the film thickness, this also results in a restriction concerning the loading with active ingredients. For this reason, monolayer films are associated with the disadvantage that the maximum possible total dose is low.

If combination products having said properties are required, a further possible problem with these thin films is the chemical incompatibility of two or more active ingredients, or else other constituents, for example, odorizers.

It is true that it is possible in principle to achieve multilayer coating by applying to an active ingredient-containing film which is already present a plurality of further layers of the same film-forming solution successively, with a drying being carried out after each application. However, in practice, this leads to the layers which are already present in each case being attacked or dissolved by the solvents in the polymer solution which is applied subsequently. This may on the one hand interfere with the production process, and on the other hand it prevents the formation of genuine multilayer systems in which the individual layers are separate from one another. It is true that dissolution of the layer produced first could be prevented by inducing certain crystallization processes therein. However, this would be associated with an unwanted reduction in the solubility of the film layers in aqueous solutions, which in turn has an adverse effect on the release of active ingredient.

SUMMARY OF THE INVENTION

It was therefore an object of the present invention to provide a composition for delivery of pharmacological or other active ingredients, which, while having compact dimensions, makes it possible for the loading with active ingredient to be high and, at the same time, the release at the site of administration to be rapid. It is particularly intended that such a composition be readily soluble in aqueous media, for example in body fluids. An additional requirement was that such a composition also makes it possible for mutually incompatible active ingredients or other constituents to be administered together. It was further intended to indicate a process of low complexity with which it is possible to produce the composition.

The object is surprisingly achieved by multilayer preparations in the form of films according to the invention, and the invention also pertains to further useful embodiments and advantageous production processes and applications.

The object is achieved according to the invention by the adjacent layers in a multilayer preparation in the form of films of hydrophilic polymers differing from one another in that in each case one layer is soluble in a nonaqueous solvent in which the respective adjacent layer is insoluble or only slightly soluble.

DETAILED DESCRIPTION

Such a structure makes it possible for the production process to be such that initially an active ingredient-containing film layer ("basic sheet") is produced from hydrophilic polymers present in solution, for example in water, and then another solution of film-forming polymers is applied to the basic sheet which is already present, the latter polymers being dissolved in a nonaqueous solvent in which the basic sheet produced first is insoluble or only slightly soluble. The basic sheet can consist, for example, of a polymer or polymer mixture which is soluble in water, whereas the polymer or polymer mixture for the following, adjacent sheet layer is soluble in higher alcohols or in chloroform, while the polymers of the basic layer are insoluble in these organic solvents. The fact that the polymers in the layer applied subsequently are soluble in organic solvents does not, however, preclude the latter also being readily soluble in water. Coating with a second (or with further) active ingredient-containing layer(s) on a layer which is already present is made possible in the manner described without the layer which is already present being attacked or dissolved by the solvents used to produce the adjacent film layer.

The thickness of the individual layers can be kept small because of the multilayer structure made possible thereby, with the advantage that the drying times during production can be reduced.

The multilayer systems according to the invention make it possible for the loading with active ingredient to be higher than with monolayer systems, the total loading growing in proportion to the number of layers present. This higher loading with active ingredient is achieved without the need to accept an increase in the surface of the film and a loss of compactness. The multilayer structure also makes it possible for active ingredients or other releasable constituents which are mutually chemically incompatible to be present within the same preparation but in different layers. It is possible in this way for mutually incompatible active ingredients, odorizers or other constituents to be spatially separate from one another and it is possible to manufacture combination products which would not otherwise be possible with a film-like dosage form. It is also possible by distributing incompatible constituents in different film layers to improve the stability of such pharmaceutical forms.

Since the multilayer preparations in the form of films according to the invention have a favorable ratio of surface area and volume, rapid release of active ingredient into liquid surroundings can take place by means of diffusion.

Particularly advantageous embodiments of the invention are those where the film layers are soluble in water or aqueous systems, preferably in human or animal body fluids, irrespective of the possibility that they are also soluble in nonaqueous systems. It is possible in this way to increase further the rate of release, in particular under physiological conditions. Although the dissolution time is longer with a multilayer structure than with monolayer systems, it is still sufficiently short with a suitable formulation for it not to represent the rate-determining step in the release of active ingredient.

Rapid dissolution of the preparation may also be desirable for other reasons, for example if the preparation is used to produce pharmaceutical forms used in the oral cavity. This can be achieved by selecting those film-forming polymers which are, on the one hand, soluble in water but, on the other hand, also soluble in nonaqueous or organic solvents as long as the latter property is required in order to prevent a film layer which has already been produced being dissolved when producing a further layer of the multilayer preparation.

The rate of release which can be achieved is in one embodiment of the invention characterized in that the time required for dissolution of a preparation with an area not exceeding 10 $cm^2$ in physiological fluids, or artificial simulations of such fluids, does not exceed 15 min, preferably does not exceed 5 min, particularly preferably does not exceed 1 min.

In view of one possible use of the preparations according to the invention for administering pharmacologically active substances to humans or animals, it is advantageous if they make it possible, on the basis of their structure, for release of the substances from the film layers to be brought about by dissolution of these layers by physiological fluids or artificial simulations thereof, preferably human or animal body fluids. This can take place by selecting suitable water-soluble film-forming polymers and other soluble additives, the skilled person being familiar with suitable polymers or additives.

The polymer layers of the preparation in film form according to the invention are suitable as matrix for taking up and subsequently releasing constituents of a wide variety of types. The substances preferably used in this connection are selected from the group which comprises pharmacological active ingredients, substances with refreshing effect, flavorings, odorizers and sweeteners. These substances may in each case be present singly or in combination in a particular layer, it being necessary to take account of the compatibility of these substances with one another. The film layers contain the active ingredient(s) or other constituents in dissolved, emulsified or suspended form.

Particularly preferred embodiments of the invention are those which contain at least one pharmacological active ingredient in at least one of the film layers. It is likewise possible for one or more layers also to contain active ingredient combinations. However, it is also possible and advantageous to use variants of the preparations according to the invention which contain in at least two layers substances or active ingredients which are different from one another. It is possible in this way to formulate combination products which contain mutually incompatible substances.

The layer structure can be designed to be variable within wide ranges. Thus, on the one hand, possible composites are those in which, starting from a basic layer, further layers are applied successively on one side in the manner described. On the other hand, a symmetrical structure is also possible, in which a further layer is applied to each of the two sides (upper and lower side) of a basic layer, as are, where appropriate, further layers.

In a particularly preferred embodiment, the composition is composed of two water-soluble layers, with one layer additionally being soluble in an organic solvent, or a mixture of such solvents, in which the other layer is insoluble.

Another particularly preferred composition has a structure comprising three water-soluble film layers. In this case, the two outer layers are additionally soluble in an organic solvent, or a mixture of such solvents, in which the middle layer is insoluble. The middle layer in this case corresponds—in terms of the sequence of production—to the basic layer.

Hydrophilic film-forming polymers suitable for producing the multilayer compositions in the form of films according to the invention are, in particular, those with high solubility in water, in particular various cellulose ethers, polyvinyl alcohols, polyvinyl acetate, polyvinyl pyrrolidone, also copolymers of the polymers mentioned, and alginates, gelatin and various other substances which are known to the skilled person and which may be of synthetic, semisynthetic or natural origin.

Particularly preferred compositions are those in which the basic layer is composed of polyvinyl alcohol or mixtures thereof, for example of a partially hydrolyzed polyvinyl alcohol of low viscosity (Mowiol® 8-88, supplied by Clariant). Polyvinyl alcohols are readily soluble in water but not, for example, in thanol. The latter solvent can therefore be used according to the invention to apply a further film layer to this basic layer of polyvinyl alcohol.

Further preferred embodiments of the invention are those in which the basic layer is produced using cellulose ethers, preferably hydroxymethylpropylcellulose, or mixtures of cellulose ethers. Apart from the use mentioned for producing the basic layer, it is also possible—when an appropriately different sequence applies to the production of the multilayer preparations—to use polyvinyl alcohols or cellulose ethers for producing the subsequent (adjacent) layers.

In further preferred embodiments, one or more further film layers of the multilayer preparation according to the invention are produced using polyvinylpyrrolidone as hydrophilic, water-soluble film-forming polymer, for example Kollidon® (supplied by BASF).

The properties of the preparations according to the invention can be optimized and adapted to the particular requirements by adding auxiliaries or additives. These include, for example, plasticizers, pigments, disintegration promoters, wetting agents, absorption- or permeation-promoting substances, structuring agents and texture modifiers, selection of the suitable additions being familiar to the skilled person. The multilayer film preparations according to the invention preferably have a thickness of at least 100 μm, particularly preferably a thickness of at least 150 μm.

The multilayer preparations in the form of films can be produced in a simple, time-saving and cost-efficient way by the processes proposed according to the invention. For this purpose, initially a polymer solution which contains the desired active ingredients, where appropriate together with auxiliaries, is produced. This solution is coated onto an inert processing sheet made of plastic or metal, which can take place by knife or roller application or spraying processes. Drying subsequently results in an initial film, also called basic layer. In the next step, a further active ingredient-containing polymer solution is applied to this basic layer, using the same processes, this polymer solution being produced using a solvent or solvent mixture which does not attack or dissolve the initial layer. Drying is then repeated, to result in a bilayer composite. It is possible subsequently to apply to this bilayer composite one or more further layers, taking account of the teaching according to the invention concerning the selection of the solvents. Another possibility arises if the bilayer composite is detached from the processing sheet, after which the underside, which is as yet uncoated, of the initial film can likewise be coated with a polymer film in the way described, so that a three-layer composite is obtained. The third layer added in this case can have either the same composition as the second, so that a symmetrical structure results, or a different one. However, it is necessary in each case for the polymer or polymers in this third layer to be, according to the teaching of the invention, in a solvent or mixture thereof which does not attack or dissolve the initial layer.

In another production process according to the invention, the first layer is produced starting from a polymer melt which contains the desired active ingredients and, where appropriate, auxiliaries or additives. The application of the melt to an inert processing sheet or other inert substrate is preferably effected by knife or roller application, spraying or extrusion processes. Cooling and/or drying thereof then results in an initial film (also called basic layer). Coating of this initial film with further active ingredient-containing polymer films to produce a multilayer preparation takes place starting from polymer solutions in the manner described previously, it also being necessary in this case to take account, in the selection of the polymers and solvents, of the fact that the latter must not attack or dissolve the initial layer or, where appropriate, the other film layers already present.

The processes according to the invention can be carried out both continuously and batchwise. The inert substrates used for continuous processes are preferably processing sheets or metal sheets or strips, whereas in batchwise processes it is possible in principle to use any inert substrates. The preparations according to the invention are preferably suitable for delivering active pharmaceutical ingredients to human or animal body fluids, or else artificial simulations thereof. They can be used particularly advantageously for administering pharmacological active ingredients or other substances in the oral, nasal or pharyngeal cavity or other body orifices or body cavities in the human or animal body, with particular preference for oral administration. A further advantageous use of the preparations according to the invention also derives from the fact that they are suitable for producing pharmaceutical preparations for medical therapy or prophylaxis of diseases in humans or animals, preferably pharmaceutical preparations for oral administration.

The following example is presented to explain the invention:

EXAMPLE

A partially hydrolyzed polyvinyl alcohol of low viscosity (Mowiol® 8-88, supplied by Clariant) is dissolved in hot water. Addition of suitable auxiliaries such as plasticizers, pigments, disintegration promoters and similar additives known to the skilled person, and the active ingredients, produces therefrom a viscous composition which is coated onto an inert substrate. Drying results in an initial film A which is easy to handle and is readily soluble in water. The dried initial film has the following composition:

28.6% by weight of Mowiol® 8-88,
7.9% by weight of titanium dioxide,
37.2% by weight of silicon dioxide,
11.5% by weight of polyethylene glycol 400,
4.6% by weight of polyethylene glycol 4000 and
10.2% by weight of sorbitol.

A second composition is then produced for the second layer B based on polyvinylpyrrolidone (Kollidon®; supplied by BASF), dissolving the film-forming polymer in ethanol. This second composition likewise contains active ingredient(s) and, where appropriate, suitable auxiliaries similar to the composition of the first layer.

The dried layer B has the following composition:

32.8% by weight of polyvinylpyrrolidone,
11.5% by weight of hydroxypropylcellulose,
6.6% by weight of titanium dioxide,
32.8% by weight of silicon dioxide and
16.4% by weight of polyethyleneglycol.

The initial Mowiol® film is insoluble in the solvent (ethanol) chosen for the polymer of th second layer B and therefore shows inert behavior towards this second composition, which can therefore be applied to the initial film.

Drying once again results in a bilayer film composite which has the layer sequence A-B and is soluble in aqueous solvent systems because both layer components are soluble in water.

After this bilayer preparation has been detached from the inert substrate it can, if desired, be coated with a further film on the still free underside of the initial film. It is possible to use for this purpose likewise the polymer solution used to produce layer B because this does not dissolve the initial layer. This results in a three-layer composite with the layer sequence B-A-B. This three-layer preparation is also readily soluble in aqueous systems. Overall, it is possible in such a three-layer system to administer three times the amount of active ingredient based on the maximum possible amount of active ingredient with which a monolayer film preparation can be loaded. Dissolution times of 60 s or less can be achieved under in vivo conditions by suitable formulations with film sections with a size of 15×15 mm.

What is claimed is:

1. A multilayer preparation in the form of films of hydrophilic polymers for rapid release of substances present in the film layers into liquid surroundings, consisting essentially of:
a composite formed from at least two film layers, adjacent film layers being different from one another in that in each case one of said layers is soluble in a nonaqueous solvent in which the respective adjacent layer is insoluble or only slightly soluble, and the layer soluble in a nonaqueous solvent is formed from polyvinylpyrrolidone or a mixture comprising polyvinylpyrrolidone, and the insoluble or only slightly soluble adjacent layer is formed from polyvinyl alcohol or a mixture comprising polyvinyl alcohol.

2. The preparation according to claim 1, wherein the film layers are soluble in water, aqueous fluids, human fluids or animal fluids, irrespective of the solubility of the film layers in nonaqueous systems.

3. The preparation according to claim 1, wherein the substances which can be released from the film layer are selected from the group consisting of pharmaceutically active ingredients, substances with refreshing effect, flavoring, odorizers and sweeteners.

4. The preparation according to claim 1, wherein the release of the substances from the film layers is brought about by dissolution of these layers by physiological liquids, artificial simulations of physiological liquids, human body fluids or animal body fluids.

5. The preparation according to claim 1, wherein the time required for dissolution of a preparation with an area not exceeding 10 cm$^2$ in physiological fluids, or artificial simulations of such fluids, does not exceed 15 min.

6. The preparation according to claim 1, wherein at least one layer contains at least one pharmacologically active substance.

7. The preparation according to claim 1, wherein at least two layers contain the same substance, the same pharmacologically active ingredient, or the same mixture of these substances.

8. The preparation according to claim 1, wherein at least two layers contain releasable substances or pharmacologically active ingredients which are different from one another.

9. The preparation according to claim 1, wherein the preparation is composed of two water-soluble layers, with one layer additionally being soluble in at least one organic solvent, in which the other layer is insoluble.

10. The preparation according to claim 1, wherein the preparation is composed of three water-soluble layers, with two outer layers additionally being soluble in at least one organic solvent, in which the middle layer is insoluble.

11. The preparation according to claim 1, which further comprises hydrophilic film-forming polymers selected from the group consisting of cellulose ethers, polyvinyl acetate, a copolymer of a cellulose ether, a copolymer of polyvinyl acetate, polyethylene glycols, alginates, gelatin and other substances of synthetic, semisynthetic or natural origin.

12. The preparation according to claim 1, wherein at least one of the layers contains auxiliaries or additives which are selected from the group consisting of plasticizers, pigments, disintegration promoters, wetting agents, absorption- or permeation-promoting substances, structuring agents and texture modifiers.

13. The preparation according to claim 1, wherein the thickness of the multilayer preparation in the form of films is at least 100 μm.

14. The preparation according to claim 1, wherein the time required for dissolution of a preparation with an area not extending 10 cm$^2$ in physiological fluids, or artificial simulations of such fluids, does not exceed 5 min.

15. The preparation according to claim 1, wherein the time required for dissolution of a preparation with an area not exceeding 10 cm$^2$ in physiological fluids, or artificial simulations of such fluids, does not exceed 1 min.

16. The preparation according to claim 1, wherein the thickness of the multilayer preparation in the form of films is at least 150 μm.

17. A multilayer preparation in the form of films of hydrophilic polymers for rapid release of substances present in the film layers into liquid surroundings, consisting of:
a composite formed from at least two film layers, adjacent film layers being different from one another in that in each case one of said layers is soluble in a nonaqueous solvent in which the respective adjacent layer is insoluble or only slightly soluble, and the layer soluble in a nonaqueous solvent is formed from polyvinylpyrrolidone or a mixture comprising polyvinylpyrrolidone, and the insoluble or only slightly soluble adjacent layer is formed from polyvinyl alcohol or a mixture comprising polyvinyl alcohol.

18. The preparation according to claim 17, wherein the film layers are soluble in water, aqueous fluids, human fluids or animal fluids, irrespective of the solubility of the film layers in nonaqueous systems.

19. The preparation according to claim 17, wherein the substances which can be released from the film layer are selected from the group consisting of pharmaceutically active ingredients, substances with refreshing effect, flavoring, odorizers and sweeteners.

20. The preparation according to claim 17, wherein the release of the substances from the film layers is brought about by dissolution of these layers by physiological liquids, artificial simulations of physiological liquids, human body fluids or animal body fluids.

21. The preparation according to claim 17, wherein the time required for dissolution of a preparation with an area not exceeding 10 cm$^2$ in physiological fluids, or artificial simulations of such fluids, does not exceed 15 min.

22. The preparation according to claim 17, wherein at least one layer contains at least one pharmacologically active substance.

23. The preparation according to claim 17, wherein at least two layers contain the same substance, the same pharmacologically active ingredient, or the same mixture of these substances.

24. The preparation according to claim 17, wherein at least two layers contain releasable substances or pharmacologically active ingredients which are different from one another.

25. The preparation according to claim 17, wherein the preparation is composed of two water-soluble layers, with one layer additionally being soluble in at least one organic solvent, in which the other layer is insoluble.

26. The preparation according to claim 17, wherein the preparation is composed of three water-soluble layers, with the two outer layers additionally being soluble in at least one organic solvent, in which the middle layer is soluble.

27. The preparation according to claim 17, which further comprises hydrophilic film-forming polymers selected from the group consisting of cellulose ethers, polyvinyl acetate, a copolymer of a cellulose ether, a copolymer of polyvinyl acetate, polyethylene glycols, alginates, gelatin and other substances of synthetic, semisynthetic or natural origin.

28. The preparation according to claim 17, wherein at least one of the layers contains auxiliaries or additives which are selected from the group consisting of plasticizers, pigments, disintegration promoters, wetting agents, absorption- or permeation-promoting substances, structuring agents and texture modifiers.

29. The preparation according to claim 17, wherein the thickness of the multilayer preparation in the form of films is at least 100 μm.

30. The preparation according to claim 17, wherein the time required for dissolution of a preparation with an area not exceeding 10 $cm^2$ in physiological fluids, or artificial simulations of such fluids, does not exceed 1 min.

31. The preparation according to claim 17, wherein the time required for dissolution of a preparation with an area not exceeding 10 $cm^2$ in physiological fluids, or artificial simulations of such fluids, does not exceed 1 min.

32. The preparation according to claim 17, wherein the thickness of the multilayer preparation in the form of films is at least 150 μm.

* * * * *